United States Patent [19]

Duhamel et al.

[11] Patent Number: 5,786,494
[45] Date of Patent: Jul. 28, 1998

[54] PROCESS FOR THE SYNTHESIS OF α-SUBSTITUTED ACRYLIC ACIDS AND THEIR APPLICATION

[75] Inventors: Pierre Duhamel; Lucette Duhamel, both of Mont Saint Aignan; Denis Danvy, Yvetot; Thierry Monteil, Mont Saint Aignan; Jeanne-Marie Lecomte; Jean-Charles Schwartz, both of Paris, all of France

[73] Assignee: Societe Civile Bioprojet, Paris, France

[21] Appl. No.: 609,209

[22] Filed: Mar. 1, 1996

[30] Foreign Application Priority Data

Mar. 3, 1995 [FR] France ..................... 95 02494

[51] Int. Cl.⁶ ..................... C07D 317/54; C07C 51/38
[52] U.S. Cl. ..................... 549/447; 562/479; 562/495
[58] Field of Search ..................... 549/447; 562/479, 562/495

[56] References Cited

FOREIGN PATENT DOCUMENTS

0419327 A1 3/1991 European Pat. Off. .
0539848 A1 5/1992 European Pat. Off. .

*Primary Examiner*—Ba K. Trinh
*Attorney, Agent, or Firm*—Larson & Taylor

[57] ABSTRACT

Process for the synthesis of a-substituted acrylic acids and their application.

Process for the synthesis of a-substituted acrylic acids of general formula (I) and their application to the synthesis of N-(mercaptoacyl) aminoacid derivatives of formula (II).

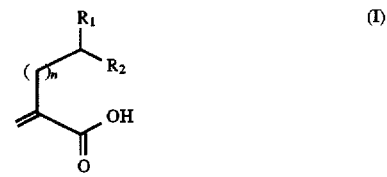

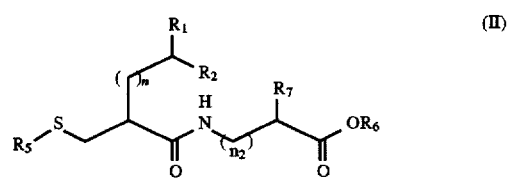

11 Claims, No Drawings

PROCESS FOR THE SYNTHESIS OF α-SUBSTITUTED ACRYLIC ACIDS AND THEIR APPLICATION

The present invention relates to a process for the synthesis of α-substituted acrylic acids and to their application to the synthesis of N- (mercaptoacyl) aminoacid derivatives.

It relates more particularly to a new process for the synthesis of α-substituted acrylic acids of general formula (I)

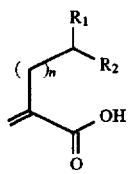

in which $R^1$ denotes a hydrogen atom; an alkyl group; a cycloalkyl group; a phenyl group optionally mono- or polysubstituted by a halogen atom, a trifluoromethyl group, a nitro group, a cyano group, an amino group, a dimethylamino group, a hydroxyl group, a lower alkoxy group, a phenoxy group, a benzyloxy group, a methylthio group, a phenyl group, a lower alkyl group, a lower phenylalkylene group; an alpha- and beta-naphthyl group or a group

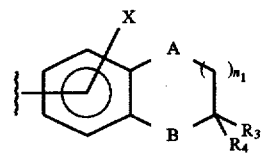

where

A is a carbon atom, an oxygen atom, a sulphur atom or a nitrogen atom,

B denotes one of the abovementioned atoms as defined for A.

$n_1$ is equal to 0 or 1,

X denotes a hydrogen atom, a halogen atom, a hydroxyl group, a lower alkoxy group or a trifluoromethyl group, $R_3$ denotes a hydrogen atom, a phenyl group, a lower alkyl group, a halogen atom or a trifluoromethyl group, $R_4$ also denotes a hydrogen atom or one of the abovementioned groups in the definition of $R_3$, $R_2$ denotes a hydrogen atom or one of the abovementioned groups in the definition of $R_1$ and n varies from 0 to 10.

The derivatives of formula (I) which are obtained according to the process of the invention are, more particularly, useful in the synthesis of N-(mercapto-acyl) aminoacids of formula (II)

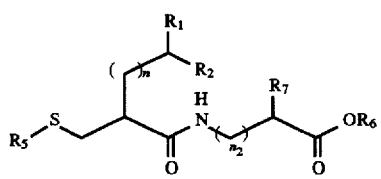

in which $R_1$ and $R_2$ have the same meaning as in formula (I);

$R_5$ denotes a hydrogen atom, a linear or branched aliphatic acyl radical or an aromatic acyl radical;

$R_6$ denotes a hydrogen atom, a lower alkyl group, a phenyl radical or a lower phenylalkylene group;

$R_7$ denotes a hydrogen atom, a lower alkyl group, a lower hydroxyalkylene group, a phenyl group, a lower phenyl-alkylene group, a lower hydroxyphenylalkylene group, a lower aminoalkylene group, a lower guanidinoalkylene group, a lower mercaptoalkylene group, a lower alkyl lower thioalkylene group, a lower imidazolylalkylene group, a lower indolylalkylene group, a lower carbamyl-alkylene group or a lower carboxyalkylene group;

n and $n_2$ vary from 0 to 10.

A lower alkyl group is intended to mean alkyl groups with a linear or branched chain, containing from 1 to 6 carbon atoms and, preferably, 1 to 4 carbon atoms.

A lower alkylene group is intended to mean alkylene groups containing from 1 to 6 carbon atoms and, preferably, 1 to 4 carbon atoms.

A lower alkoxy group is intended to mean an alkoxy group containing a linear or branched chain of 1 to 6 carbon atoms.

An alkyl group is intended to mean alkyl groups with a linear or branched chain, containing 1 to 20 carbon atoms.

A cycloalkyl group is intended to mean a saturated ring of 3 to 7 carbon atoms.

The preferred compounds of formula (II) are the compounds corresponding to the following formulae: 1)

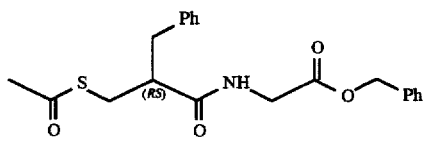

or benzyl N-(RS)-[2-acetylthiomethyl-1-oxo-3-phenyl-propyl]glycinate; 2)

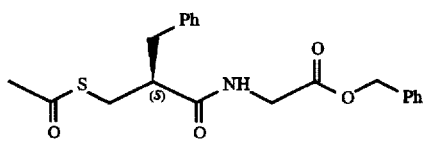

or benzyl N-(S)-[2-acetylthiomethyl-1-oxo-3-phenyl-propyl]glycinate; 3)

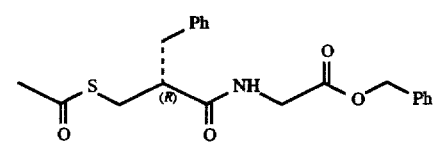

or benzyl N-(R)-[2-acetylthiomethyl-1-oxo-3-phenyl-propyl]glycinate; 4)

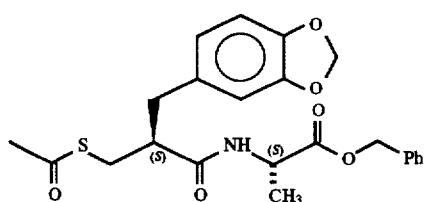

or benzyl N-(S)-[2-acetylthiomethyl-1-oxo-3- (3,4-methylenedioxyphenyl) propyl]-(S)-alaninate. 5)

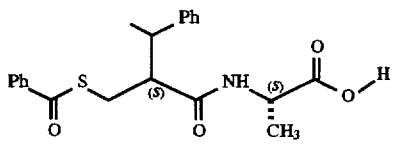

or N-[(2S,3R)-2-benzoylthiomethyl-1-oxo-3-phenylbutyl]-(S)-alanine.

The compounds of formula (II) have advantageous pharmacological properties. In particular, they have an inhibiting action on some enzymes, like neutral endopeptidase (EC 3.4.24.11) and the enzyme for conversion of angiotensin (EC 3.4.15.1). Administration of the compounds of formula (II) makes it therefore possible to reduce or to suppress the activity of these enzymes, which are responsible, respectively, for the inactivation of encephalins, of the natriuretic atrial factor and for the conversion of angiotensin I to angiotensin II. In therapeutics, these compounds exert intestinal, antisecretory or antihypertensive activities and are employed in the treatment of chronic cardiac insufficiency. In addition, such compounds may also be employed in the treatment of osteoporosis (PCT Int. Appl. WO. 94/21,242).

The compounds of formula (II) and, more particularly the compound of formula (III), their preparation and their use in therapeutics have been described in European Patent No. 038 758.

The compounds of formula (II) and, more particularly the compounds of formulae (IV) and (V), their preparation and their use in therapeutics have been described in French Patent No. 2,623,498.

The compounds of formula (II) and, more particularly the compound of formula (VI), their preparation and their use in therapeutics have been described in European Patent No. 0 419 327.

Few specific processes for industrial synthesis of the derivatives of formula (I) have been described. European Patent No. 0 419 327 and European Patent Application No. 0 539 848 are known, involving a Mannich reaction on a malonic monoacid. However, this route does not lead directly to the acrylic acids of formula (I) but to the corresponding esters, and does so with mediocre yields. European Patent Application No. 0 539 848 is also known, involving a Wittig reaction between formaldehyde and the anion of an alkylated phosphonoester to give access to acrylic esters. However, this route requires the presence of a strong base, such as sodium hydride, and the yields are mediocre.

The Applicant has now discovered a process for industrial synthesis of α-substituted acrylic acids of formula (I), which is particularly advantageous because, on the one hand, of its ease of use and, on the other hand, of the fact that it employs low-cost raw materials, leading directly to the acrylic acids of formula (I) and doing so with high yields.

According to an essential characteristic of the process in accordance with the invention, the latter employs as raw materials the esters of alkylated malonic acids of formula (VIII)

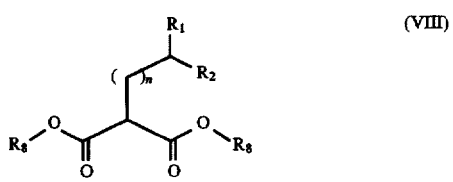

in which n, $R_1$ and $R_2$ have the same meaning as in formula (I) and $R_8$ denotes an alkyl chain containing from 1 to 4 carbon atoms.

The alkylated malonic esters of formula (VIII) can be obtained by reacting a halide of formula (IX)

in which n, $R_1$ and $R_2$ have the same meaning as in formula (I) and Y denotes a halogen atom, with an ester of malonic acid, of formula (X)

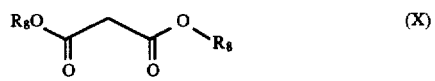

in which $R_8$ has the abovementioned definition, in the presence of an alcoholic solution of an alkali metal.

The halide of formula (IX) employed for performing the malonic synthesis of the compounds of formula (VIII) is preferably a chlorine, bromine or iodine derivative.

The alcoholic solution of an alkali metal in the presence of which the malonic synthesis of the derivatives of formula (VIII) is performed may be, for example, a solution of sodium in ethanol or a solution of sodium in methanol.

The malonic esters of formula (VIII) can also be obtained by a Knoevenagel condensation of a carbonyl compound of formula (XI) or (XI')

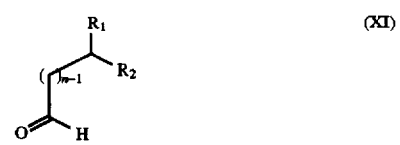

in which $R_1$ and $R_2$ have the same definition as in formula (I) and n varies from 1 to 10, with a malonic acid ester of formula (X) in the presence of a base and of a carboxylic acid, by performing an azeotropic entrainment in an organic solvent such as toluene, to form the esters of formula (XII) or (XII')

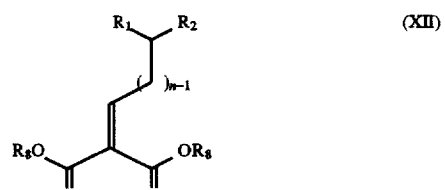

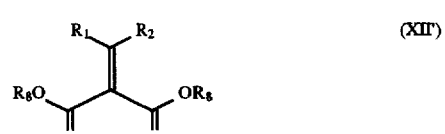

in which $R_1$, $R_2$ and $R_8$ have the abovementioned meanings and n varies from 1 to 10.

The base employed for the Knoevenagel reaction is preferably piperidine, and the carboxylic acid employed for this same reaction may be, for example, acetic acid or benzoic acid.

The esters of formula (VIII) are obtained by catalytic hydrogenation of the esters of formula (XII) or (XII'). The hydrogenation catalyst may be, for example, palladized charcoal.

The process for the synthesis of the acrylic acids of formula (I) in accordance with the invention therefore consists, first of all, in preparing the malonic esters of formula (VIII), either by starting from a halide of formula (IX) or by starting from a carbonyl compound of formula (XI) or (XI') by a Knoevenagel reaction, as indicated above.

The malonic esters of formula (VIII) are next saponified with a basic aqueous solution such as an aqueous solution of sodium hydroxide, to produce the diacids of formula (XIII)

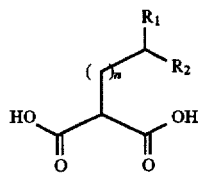

(XIII)

in which n, $R_1$ and $R_2$ have the same definition as in formula (I).

The diacids of formula (XIII) are subjected to a Mannich reaction with an organic base and formaldehyde, to produce the acrylic acids of formula (I).

The base employed for performing the Mannich reaction is preferably selected from diethylamine, dimethylamine and piperidine.

The process in accordance with the invention is more particularly suited for the preparation of the acrylic acids of formula

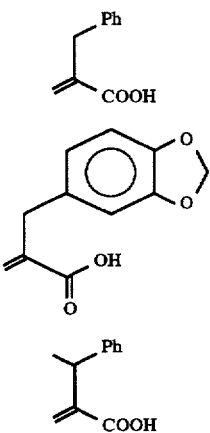

(Ia)

(Ib)

(Ic)

When applied to the preparation of the acrylic acid (Ia) or (Ib) and if the preparation of the malonic ester (VIII) is undertaken by starting from a carbonyl compound (XI), the process in accordance with the invention consists:

- in performing a Knoevenagel condensation of benzaldehyde (if it involves preparing the acid (Ia)) or of piperonal (if it involves preparing the acid (Ib)) with a malonate of formula (X), in the presence of a base such as piperidine and of an organic acid such as acetic acid, in a solvent such as toluene,
- in subjecting the ester formed to a catalytic hydrogenation in the presence, for example, of palladized charcoal,
- in saponifying the diester obtained, with an alkaline aqueous solution, for example an aqueous solution of sodium hydroxide,
- in liberating the diacid of formula (XIIIa) or (XIIIb)

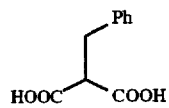

(XIIIa)

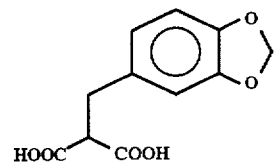

(XIIIb)

by acidification, and in then extracting it with a solvent such as ethyl acetate, and

- in subjecting the diacid to the action of an organic base such as diethylamine and of formaldehyde to form the acid (Ia) or (Ib).

When applied to the preparation of the acrylic acid (Ic) and if the preparation of the malonic ester (VIII) is undertaken by starting from a halide of formula (IX), the process in accordance with the invention consists:

- in reacting a halide (IX), for example 1-chloro-1-phenylethane with a malonate of formula (X), in the presence of an alcoholic solution of an alkali metal, such as a solution of sodium in ethanol or in methanol,
- in saponifying the diester obtained, with an alkaline aqueous solution, for example an aqueous solution of sodium hydroxide,
- in liberating, by acidification, the diacid of formula (XIIIc)

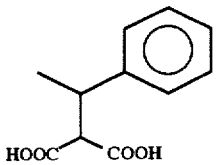

(XIIIc)

and then extracting it with a solvent such as ethyl acetate, and

- in subjecting the diacid to the action of an organic base such as diethylamine and of formaldehyde, to form the acid (Ic).

The acrylic acids of formula (I) which are obtained by the process in accordance with the present invention find a particularly advantageous use in the synthesis of the N-(mercaptoacyl)aminoacids of formula (II). They are particularly suited for the synthesis of the amino acid derivatives of formulae (III), (IV), (V), (VI) and (VII).

The preparation of N-(mercaptoacyl)aminoacids from acrylic acids is known and is described, for example, in European Patent No. 0 419 327.

N-(Mercaptoacyl)aminoacids can be obtained by this succession of stages:

- acrylic acid is subjected to a Michael addition with a sulphur derivative of formula $R_5$—SH to form the acid of formula (XIV)

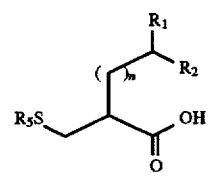

(XIV)

where $R_1$, $R_2$ and $R_5$ have the meanings which were given in formula (II)

- the acid of formula (XIV) is optionally resolved,
- the acid of formula (XIV) in racemic or optically pure form is coupled with an aminoester of formula (XV)

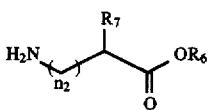

where $R_6$ and $R_7$ and $n_2$ have the meanings which were given in formula (II), in the presence of a coupling agent such as dicyclo hexylcarbodiimide, to form the derivatives of formula (II)

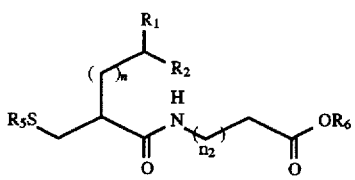

A few examples illustrating the use of the process in accordance with the invention will be given below, no limitation being implied.

EXAMPLE 1:

Benzylacrylic acid (Ia)
Route A: Synthesis from diethyl malonate
Stage 1: Diethyl benzylidenemalonate.

Into a one-liter three-necked conical flask are introduced 60 g (565.39 mmol) of benzaldehyde, 90.56 g (565.39 mmol) of diethyl malonate, 3.85 g (45.21 mmol) of piperidine, 130 ml of toluene and 2.71 g (45.16 mmol) of acetic acid.

The three-necked flask is fitted with a Dean & Stark unit and a condenser. It is stirred and heated to reflux for 3 h 30 min. 12.7 ml of water are recovered and the reaction mixture is then allowed to return to ambient temperature.

Stage 2: Diethyl benzylmalonate

The above solution is transferred to a 450-ml hydrogenator. 3 g of 10% palladized charcoal are introduced and the assembly is purged 3 times with hydrogen. Hydrogen is introduced up to a pressure of 15 bars. The initial temperature is 27° C.

After 1 h 15 min of stirring the temperature is 39° C. and the pressure is at 8 bars.

The pressure is increased again to 12 bars with hydrogen and heating to approximately 55° C. is applied for 2 hours.

The mixture is next cooled to ambient temperature and then decompressed.

The solution is filtered on a glass sinter of porosity No. 4.
Stage 3: Benzylmalonic acid (XIIIa)

The above solution is transferred to a one-liter three-necked conical flask and 117 ml (1.412 moles) of an aqueous solution of sodium hydroxide at a concentration of 35 % and 117 ml of water are added in succession.

Vigorous stirring is applied and the mixture is refluxed for 2 h 45 min.

The reaction mixture is next returned to ambient temperature. It is transferred to a separating funnel and the organic phase is removed.

The basic aqueous phase is cooled to approximately 10° C., stirred vigorously and acidified with 115 ml of 35% HCl (pH=1).

It is extracted with ethyl acetate: once with 100 ml and once with 70 ml. These two phases are combined.
Stage 4: Benzylacrylic acid (Ia)

The above solution is cooled to approximately 10° C. 58.3 ml (564.63 mmol) of diethylamine are added with stirring without exceeding 30° C. in the mixture, followed by 26.8 g (848.66 mmol) of paraformaldehyde. The mixture is refluxed for 30 minutes. $CO_2$ release has then ended and the solution is clear.

The temperature is 61° C. at the beginning of the reflux and reaches 72° C. at the end. The mixture is then cooled to approximately 10° C., diluted with 50 ml of water and acidified with 50 ml of 35% HCl (pH=1) without exceeding 20° C. in the mixture.

The mixture is transferred to a separating funnel and the aqueous phase is removed.

The ethyl acetate phase is concentrated in a rotary evaporator until an oil is obtained. 100 ml of water are then added and the evaporation of ethyl acetate is finished. A precipitation of the acid is observed. The suspension is agitated, cooled to 10° C., filtered and washed twice with 100 ml of water.

The salt is dried over $P_2O_5$ and KOH to constant mass.

77.3 g of white salt are obtained. Overall yield for these four stages: 84%. Melting point: 69° C. (Köfler). $^1$H NMR ($CDCl_3$): (200 MHz): 11.7 (broad singlet, 1H), 7.4 to 7.15 (unresolved bands, 5H), 6.45 (singlet, 1H), 5.6 (doublet, IR, J=1.2 Hz), 3.65 (singlet, 2H). Route B: Synthesis from dimethyl malonate Stage 1: Dimethyl benzylidenemalonate Into a one-liter three-necked conical flask are introduced in succession 60 g (565.39 mmol) of benzaldehyde, 77 g of dimethyl malonate (565.32 mmol), 3.85 g of piperidine (45.21 mmol), 130 ml of toluene and 2.71 g (45.16 mmol) of acetic acid.

The three-necked flask is fitted with a Dean & Stark unit and heated to reflux, with stirring, for 3 hours.

15 ml of water are collected and the reaction mixture is then allowed to return to ambient temperature.
Stage 2: Dimethyl benzylmalonate The above solution is transferred to a 450-ml hydrogenator. 3 g of 10% palladized charcoal are introduced and the assembly is purged 3 times with hydrogen. It is agitated and hydrogen is introduced to a pressure of 15 bars.

The initial temperature is 22° C.

After 20 minutes' agitation, the temperature reaches 56° C. and the pressure is at 6 bars. The pressure is increased again to a pressure of 15 bars with hydrogen and a temperature of approximately 55° C. is maintained for 1 h 30 min. The mixture is next cooled to ambient temperature and then decompressed. The solution is filtered on a glass sinter of porosity No.4.
Stage 3: Benzylmalonic acid (XIIIa)

The above solution is transferred to a one-liter three-necked conical flask and 117 ml (1.412 moles) of 35% NaOH and 117 ml of water are added in succession.

The mixture is stirred vigorously and refluxed for 3 hours.

After returning to ambient temperature the mixture is poured into a separating funnel. The organic phase is removed and the aqueous phase is cooled, agitated vigorously and acidified with 115 ml of 35% HCl (pH=1).

It is extracted with ethyl acetate: once with 100 ml and once with 70 ml. These two phases are combined.
Stage 4: Benzylacrylic acid (Ia)

The above solution is cooled in an iced water bath. It is stirred and 58.3 ml (564.63 mmol) of diethylamine are added without exceeding 30° C. in the mixture, followed by 26.8 g (848.66 mmol) of paraformaldehyde.

The mixture is refluxed for 30 minutes. $CO_2$ release has then ended and the mixture has become clear. It is then cooled with an iced water bath, diluted with 50 ml of water and acidified with 50 ml of 35% HCl (pH=1). The acidic aqueous phase is removed and the organic phase is concentrated in a rotary evaporator until an oil is obtained. 100 ml of water are then added and the evaporation of ethyl acetate is finished. A precipitation of the acid is observed.

The suspension is agitated, cooled in an iced water bath to approximately 15° C. and filtered. The precipitate is washed twice with 100 ml of water. The precipitate is dried over $P_2O_5$ and KOH to constant mass. 71.86 g of white solid are obtained. Overall yield for these four stages: 78 % Melting point: 69° C. (Köfler)

EXAMPLE 2:

Piperonylacrylic acid (Ib)

Stage 1: Diethyl piperonylidenemalonate

Into a one-liter three-necked conical flask are introduced 50 g (333.04 mmol) of piperonal, 53.34 g (333.04 mmol) of diethyl malonate, 2.26 g (26.59 mmol) of piperidine, 110 ml of toluene and 1.6 g (26.66 mmol) of acetic acid.

The three-necked flask is fitted with a Dean & Stark unit and a condenser. It is stirred and refluxed for 3 h 30 min. 7 ml of water are recovered and the reaction mixture is then allowed to return to ambient temperature.

Stage 2: Diethyl piperonylmalonate

The above solution is transferred to a 450-ml hydrogenator.

2.5 g of 10% palladized charcoal are introduced and the assembly is purged 3 times with hydrogen. It is agitated and hydrogen is introduced to a pressure of 15 bars. The initial temperature is 20° C.

After 1 h of agitation the temperature is 29° C. and the pressure is at 10 bars. The pressure is again increased to 15 bars with hydrogen and the mixture is heated to approximately 55° C. for 2 h 30 min.

It is next cooled to ambient temperature and then decompressed.

It is filtered on a glass sinter of porosity No. 4 and rinsed with 20 ml of toluene.

Stage 3: Piperonylmalonic acid (XIIIb)

The above solution is transferred to a one-liter three-necked conical flask and 69 ml of 35% NaOH (833.17 mmol) and 69 ml of water are added in succession.

The mixture is stirred vigorously and refluxed for 3 hours.

The mixture is next returned to ambient temperature and poured into a separating funnel. The organic phase is removed, the aqueous phase is cooled with an iced water bath and is agitated vigorously. 90 ml of ethyl acetate and 70 ml of 35% HCl (pH=1) are added in succession.

The mixture is transferred to a separating funnel and the organic phase is recovered.

The aqueous phase is again extracted with 60 ml of ethyl acetate. These two phases are combined.

Stage 4: Piperonylacrylic acid (Ib)

The above solution is introduced into a 500-ml conical flask and agitated vigorously. 34.3 ml (332.19 mmol) of diethylamine are added in succession (addition over 2 minutes), the temperature then reaching 50° C., followed by 15.7 g (497.16 mmol) of paraformaldehyde.

A precipitation of the mixture is then observed. The latter is refluxed for 30 minutes. $CO_2$ release is then ended and the mixture has become clear.

The temperature is 61° C. at the beginning of the reflux and reaches 72° C. at the end. The mixture is cooled with an ice bath, diluted with 40 ml of water and acidified with 30 ml of 35% HCl. A precipitation is then observed. The precipitate is filtered off and the filtrate is transferred to a separating funnel. After the aqueous phase has been removed, the ethyl acetate phase is diluted with 60 ml of water and concentrated under vacuum in a rotary evaporator.

A precipitation is then observed. The suspension is cooled to approximately 10° C. and filtered. The two precipitates, which are washed twice with 100 ml of water, are combined. 77.06 g of solid are obtained, which is dried under vacuum over $P_2O_5$ and KOH to constant mass.

58.51 g of white solid are obtained. Overall yield for these four stages: 85%. Melting point: 130° C. (Köfler) $^1$H NMR (CDCl$_3$): 200 MHz: 10 (broad singlet, 1H), 6.8 to 6.6 (unresolved bands 3H), 6.85 (doublet, 1H, J=0.4 Hz), 5.9 (singlet,2H), 5.6 (doublet, 1H, J=1.5 Hz), 3.5 (singlet, 2H).

EXAMPLE 3:

2-(1-Phenylethyl)acrylic acid (Ic)

Stage 1: Diethyl (1-phenylethyl)malonate.

58.7 g (417.79 mmol) of 1-chloro-1-phenylethane and 280 g (1.75 moles) of diethyl malonate are introduced into a three-necked conical flask. A solution prepared from 25 g (1.086 moles) of sodium and 640 ml of ethanol is added with stirring and then this mixture is refluxed for 5 hours. The ethanol is evaporated off in a rotary evaporator and then the residue is taken up with water (150 ml) and ethyl ether (300 ml). The aqueous phase is removed and the organic phase is washed with water to neutral pH.

The ether phase is dried over magnesium sulphate, filtered and concentrated.

An oily residue is obtained which is distilled using a vane pump, in order to remove the excess diethyl malonate (60°–70° C. at 0.2 mm Hg).

The distillation residue contains diethyl (1-phenylethyl) malonate. Mass=102.5 g. Yield=92%.

Stage 2: (1-Phenylethyl)malonic acid (XIIIc)

72.5 ml (875.43 mmol) of a 35% sodium hydroxide solution and 290 ml of water are added to 92.44 g (350.15 mmol) of diethyl (1-phenylethyl)malonate (stage 1).

The mixture is refluxed for 3 hours. The reaction mixture is allowed to return to ambient temperature and the ethanol is distilled off in a rotary evaporator.

The aqueous phase is cooled and acidified with concentrated HCl to pH=1.

It is extracted with ethyl ether (twice 200 ml). The ether phases are combined, dried over magnesium sulphate, filtered and concentrated. 1-Phenylethyl-malonic acid is thus obtained in the form of white solid. Mass=70.7 g Yield=97% Melting=136° C. (Köfler).

Stage 3: 2-(1-Phenylethyl)acrylic acid (Ic)

35.1 ml (339.94 mmol) of diethylamine and 16.1 g (509.83 mmol) of paraformaldehyde are added in succession to a solution of 70.7 g (339.90 mmol) of (1-phenylethyl) malonic acid originating from stage 2 in 450 ml of ethyl acetate.

The mixture is refluxed for 30 minutes. Carbon dioxide release has then ended and the mixture has become clear.

It is cooled with an ice bath, diluted with 40 ml of water and acidified to pH=1 with 35% HCl. The aqueous phase is separated off and the organic phase diluted with 60 ml of water and concentrated under vacuum. The precipitate is filtered off and washed twice with 100 ml of water.

59.17 g of solid are obtained and are dried under vacuum over $P_2O_5$ to constant mass. Mass=53.77 g Yield=89% Melting=113° C. $^1$H NMR (CDCl$_3$)=11.2 (broad singlet, 1H), 7.45 to 7.15 (unresolved bands 5H), 6.5 (singlet, 1H), 5.75 (singlet, 1H), 4.05 (quadruplet, 1H, J=7 Hz), 1.5 (doublet, 3H, J=7 Hz).

EXAMPLES 4 to 9

The acrylic acids (I) are obtained by following the procedure of Example 3, but employing commercial diethyl malonates in the case of Examples 6, 7 and 8:

![Formula 1 structure with R1, R2, COOH and (n) subscript]

| Example | R₁ | R₂ | n | Melting (°C.) | Yield (%) from the compounds (VIII) |
|---------|----|----|---|---------------|--------------------------------------|
| 4 | CH₃ | CH₃ | 1 | Oil | 90 |
| 5 | H | (naphthyl-CH<) | 3 | 85 | 86 |
| 6 | H | H | 1 | Oil | 91 |
| 7 | H | CH₃ | 1 | Oil | 94 |
| 8 | CH₃ | CH₃ | 0 | Oil | 91 |
| 9 | H | H | 11 | <50 | 67 |

EXAMPLE 10:

Benzyl N-(RS)-[2-acetylthiomethyl-1-oxo-3-phenylpropyl]glycinate (III)

Stage 1: 2-Acetylthiamethyl-3-phenylpropanoic acid 10 g of benzylacrylic acid Ia (61.7 mmol) and 7.1 ml of thioacetic acid (1.6 eq.) are placed in a round bottom flask fitted with a condenser and a CaCl₂ trap.

The mixture is heated to 70° C. with stirring for 24 h.

The excess thioacetic acid is evaporated off under vacuum (1 mm, 60° C.).

The yellow pasty residue is taken up three times with 50 ml of ether. Each time the ether is evaporated off at normal pressure and then the residue is dried under vacuum.

These stages are intended to remove the remaining traces of thioacetic acid.

14 g of a very viscous yellow oil are obtained (Yield=95 %).

Stage 2: Benzyl N-(RS)-[2-acetylthiomethyl-1-oxo-3-phenylpropyl]glycinate (III)

10 g of 3-acetylthio-2-benzylpropanoic acid (42 mmol) in solution in 70 ml of anhydrous THF are placed in a round bottom flask fitted with a CaCl₂ trap and a magnetic stirrer.

The flask is cooled to approximately 0°–5° C. with an ice bath and the benzyl glycinate para-toluene-sulphonate salt (42 mmol) is added, followed in succession by 5.75 ml of triethylamine (42 mmol) in 80 ml of chloroform, a solution of 6.3 g (42 mmol) of hydroxy-benzotriazole in 60 ml of anhydrous THF and a solution of 8.65 g (42 mmol) of dicyclohexylcarbodiimide in 50 ml of CHCl₃.

The mixture is stirred 1 h at 0° C. and then approximately 6 h at ambient temperature.

The DCU precipitate is filtered off and the filtrate is evaporated to dryness.

The pasty residue is taken up with ethyl acetate (100 ml). The DCU which has precipitated again is filtered off. The organic phase is washed successively with once 20 ml of water, 3 times 20 ml of a saturated solution of NaHCO₃, once 20 ml of water and once 20 ml of a saturated solution of NaCl.

It is dried over sodium sulphate and evaporated to dryness.

A white solid residue is obtained, which can be recrystallized from ether.

Example for the benzyl ester: Weight=14.6 g Yield=90% m.p.=89° C. TLC (silica gel) rf (CHCl₃/MeOH/water: 9/1/sat)=0.80

We claim:

1. Process for the synthesis of α-substituted acrylic acids of formula (I)

in which

R₁ denotes a hydrogen atom, an alkyl group, a cycloalkyl group, a phenyl group optionally mono- or polysubstituted by a halogen atom, a trifluoromethyl group, a nitro group, a cyano group, an amino. group, a dimethylamino group, a hydroxyl group, a lower alkoxy group, a phenoxy group, a benzyloxy group, a methylthio group, a phenyl group, a lower alkyl group, a lower phenylalkylene group; an alpha- and beta-naphthyl group or a group

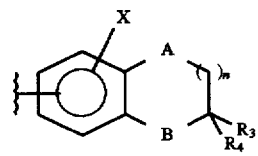

where

A is a carbon atom, an oxygen atom, a sulphur atom or a nitrogen atom,

B denotes one of the abovementioned atoms as defined for A, n₁ is equal to 0 or 1, X denotes a hydrogen atom, a halogen atom, a hydroxyl group, a lower alkoxy group or a trifluoromethyl group, R₃ denotes a hydrogen atom, a phenyl group, a lower alkyl group, a halogen atom or a trifluoromethyl group, R₄ also denotes a hydrogen atom or one of the abovementioned groups in the definition of R₃, R₂ denotes a hydrogen atom or one of the abovementioned groups in the definition of R₁ and n varies from 0 to 10, characterized in that, in succession,
a) the alkylated esters of malonic acids are prepared, of formula (VIII)

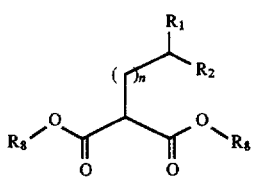  (VIII)

in which n, $R_1$ and $R_2$ have the same meaning as in formula (I) and $R_8$ denotes an alkyl chain containing from 1 to 4 carbon atoms,
the alkylated esters of ialonic acids being obtained either by reacting a halide of formula (IX)

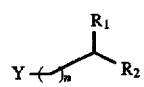  (IX)

in which n, $R_1$ and $R_2$ have the same meaning as in formula (I) and Y denotes a halogen atom, with a malonic acid ester of formula (X)

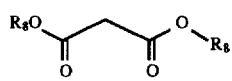  (X)

in which $R_8$ has the abovementioned definition, in the presence of an alcoholic solution of an alkali metal,
or by a Knoevenagel condensation of a carbonyl compound of formula (XI) or (XI')

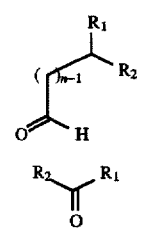  (XI)

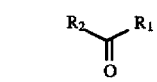  (XI')

in which $R_1$ and $R_2$ have the same definition as in formula (I) and n varies from 1 to 10, with a malonic acid ester of formula (X) in the presence of a base and of a carboxylic acid, to produce the esters of formula (XII) or (XII')

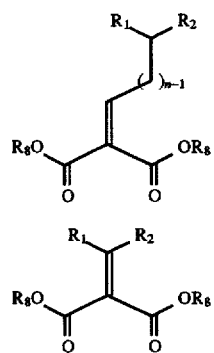

(XII)

(XII')

in which $R_1$, $R_2$ and $R_8$ have the abovementioned meanings and n varies from 1 to 10, the esters of formula (XII) or (XII') being next subjected to a catalytic hydrogenation to form the esters of formula (VIII);

b) the esters of formula (VIII) are saponified in the presence of a basic aqueous solution, to form the diacids of formula (XIII)

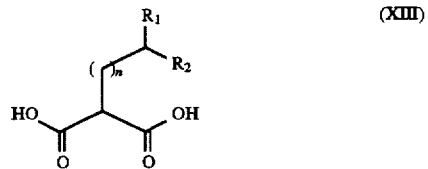  (XIII)

in which n, $R_1$ and $R_2$ have the same definition as in formula (I);

c) the diacids of formula (XIII) are subjected to a Mannich reaction with an organic base and formaldehyde to form the acrylic acids of formula (I).

2. Process according to claim 1, characterized in that the halide of formula (IX) is a chlorine, bromine or iodine derivative.

3. Process according to claim 1, characterized in that the alcoholic solution of an alkali metal is a solution of sodium in ethanol or a solution of sodium in methanol.

4. Process according to claim 1, characterized in that the base employed for the Knoevenagel reaction is piperidine.

5. Process according to claim 1, characterized in that the carboxylic acid employed for the Knoevenagel reaction is selected from acetic acid and benzoic acid.

6. Process according to claim 1, characterized in that the catalytic hydrogenation of the compounds of formulae (XII) and (XII') is performed by employing palladized charcoal as catalyst.

7. Process according to claim 1, characterized in that the basic aqueous solution employed for the saponification of the diesters of formula (VIII) is an aqueous solution of sodium hydroxide.

8. Process according to claim 1, characterized in that the base employed for the Mannich reaction is selected from diethylamine, dimethylamine and piperidine.

9. Process according to claim 1, characterized in that, when applied to the preparation of the acrylic acid of formula

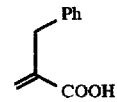  (Ia)

it consists in performing a Knoevenagel condensation of a carbonyl compound of formula (XI), benzaldehyde, with a malonate of formula (X), in the presence of a base such as piperidine and of a carboxylic acid such as acetic acid, in a solvent such as toluene, in subjecting the esters obtained to a catalytic hydrogenation, in saponifying the diesters with an alkaline aqueous solution such as an aqueous solution of sodium hydroxide, in liberating the diacid of formula (XIIIa) by acidification

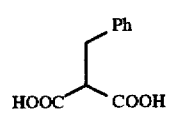  (XIIIa)

and in extracting it with an organic solvent such as ethyl acetate, and in subjecting the solution to the action of a base such as diethylamine and of formaldehyde, to give the acid of formula (Ia).

10. Process according to claim 1, characterized in that, when applied to the preparation of the acrylic acid of formula

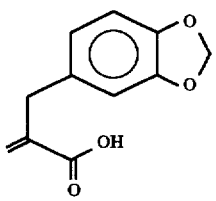
(Ib)

it consists

- in condensing a carbonyl compound of formula (XI), piperonal, according to a Knoevenagel reaction with a malonate of formula (X), in the presence of a base such as piperidine and of an organic acid such as acetic acid, in an organic solvent such as toluene,
- in subjecting the esters formed to a catalytic hydrogenation,
- in saponifying the diesters with an alkaline aqueous solution such as a solution of sodium hydroxide,
- in liberating the diacid of formula (XIIIb) by acidification

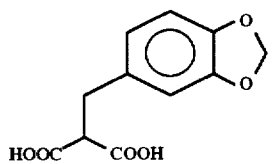
(XIIIb)

and in then extracting it with an organic solvent such as ethyl acetate, and

- in subjecting the solution to the action of a base such as diethylamine and of formaldehyde, to give the acid of formula (Ib).

11. Process according to claim 1, characterized in that, when applied to the preparation of the acrylic acid of formula

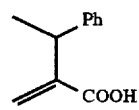
(Ic)

it consists

- in reacting a halide of formula (IX) such as a chlorine derivative in which $R_1$ is a phenyl group, $R_2$ is a methyl group, Y denotes chlorine and n=0, with a malonic ester of formula (X) in the presence of an alcoholic solution of an alkali metal, such as a solution of sodium in ethanol or in methanol,
- in saponifying the diester obtained with an alkaline aqueous solution such as an aqueous solution of sodium hydroxide,
- in liberating the diacid of formula (XIIIc)

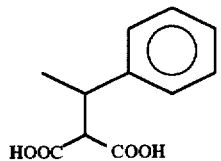
(XIIIc)

by acidification and in extracting it with an organic solvent such as ethyl acetate, and

- in subjecting the solution to the action of a base such as diethylamine and of formaldehyde, to give the acid of formula (Ic).

* * * * *